United States Patent [19]

Tovey et al.

[11] Patent Number: 5,403,342
[45] Date of Patent: Apr. 4, 1995

[54] ARTICULATING ENDOSCOPIC SURGICAL APPARATUS

[75] Inventors: H. Jonathan Tovey, Milford; Ernie Aranyi, Easton; Thomas D. Guy, Fairfield; Joseph Pasqualucci, North Haven; H. Allan Alward, Milford; Michael Smith, Middletown, all of Conn.

[73] Assignee: United States Surgical Corporation, Norwalk, Conn.

[21] Appl. No.: 80,830

[22] Filed: Jun. 21, 1993

Related U.S. Application Data

[63] Continuation-in-part of Ser. No. 872,057, Apr. 23, 1992.

[51] Int. Cl.6 ............................................. A61B 17/28
[52] U.S. Cl. .................................. 606/205; 606/206; 128/4; 128/751
[58] Field of Search ............... 606/205, 206, 207, 170, 606/174, 52, 41; 128/751, 752, 4, 7

[56] References Cited

U.S. PATENT DOCUMENTS

| | | |
|---|---|---|
| 2,113,246 | 4/1938 | Wappler . |
| 2,487,502 | 11/1949 | Willinsky . |
| 3,314,431 | 4/1967 | Smith, Jr. . |
| 3,628,212 | 11/1971 | Fannon, Jr. et al. . |
| 3,890,977 | 6/1975 | Wilson . |
| 4,665,906 | 5/1987 | Jervis . |
| 4,668,555 | 8/1987 | Wardle . |
| 4,763,669 | 8/1988 | Jaeger . |
| 4,872,456 | 10/1989 | Hasson ............................ 128/321 |
| 4,880,015 | 11/1989 | Nierman . |
| 4,944,741 | 7/1990 | Hasson . |
| 4,945,920 | 8/1990 | Clossick . |
| 5,152,279 | 10/1992 | Wilk . |
| 5,174,300 | 12/1992 | Bales et al. . |
| 5,209,747 | 5/1993 | Knoepfler ............................ 606/16 |
| 5,254,130 | 10/1993 | Ponlet et al. ....................... 606/206 |
| 5,258,006 | 11/1993 | Ridell et al. ........................ 606/205 |

FOREIGN PATENT DOCUMENTS

| | | |
|---|---|---|
| 484671 | 5/1992 | European Pat. Off. ............ 606/205 |
| 3704094 | 8/1988 | Germany . |
| 4024636 | 2/1992 | Germany . |
| 2151142 | 7/1985 | United Kingdom . |
| 990220 | 1/1983 | U.S.S.R. . |
| WO9102493 | 3/1991 | WIPO . |
| WO9320760 | 10/1993 | WIPO . |

OTHER PUBLICATIONS

"Levy Articulating Retractor", Surgical Products, p. 33, Jun. 1992 Edition.

*Primary Examiner*—Richard J. Apley
*Assistant Examiner*—Beverly A. Meindl

[57] ABSTRACT

A surgical instrument is provided for performing a variety of endoscopic or laparoscopic procedures including the electrocauterization of tissue. The instrument includes a handle assembly, a tubular body extending from the handle assembly therein defining a longitudinal axis, a tool assembly associated with a distal end of the tubular body including a tool base and tool members, an electrical connector electrically associated with the tool members, electrical insulation being provided in association with electrical conducting components, a first mechanism for effectuating remote articulation of the tool assembly with respect to the longitudinal axis of the tubular body, and a second mechanism for effectuating remote rotation of the tool assembly about the longitudinal axis of the tubular body.

36 Claims, 13 Drawing Sheets

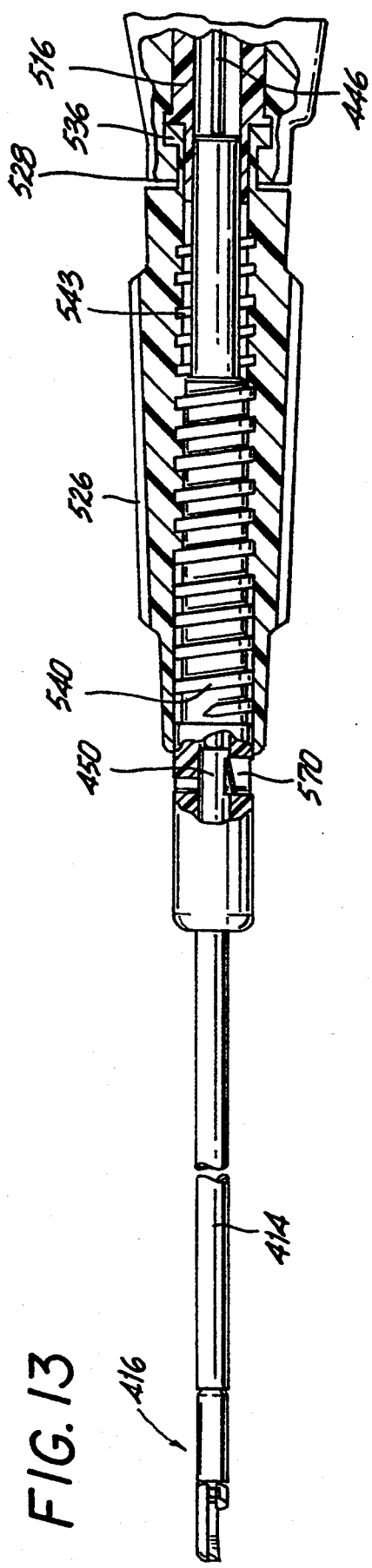
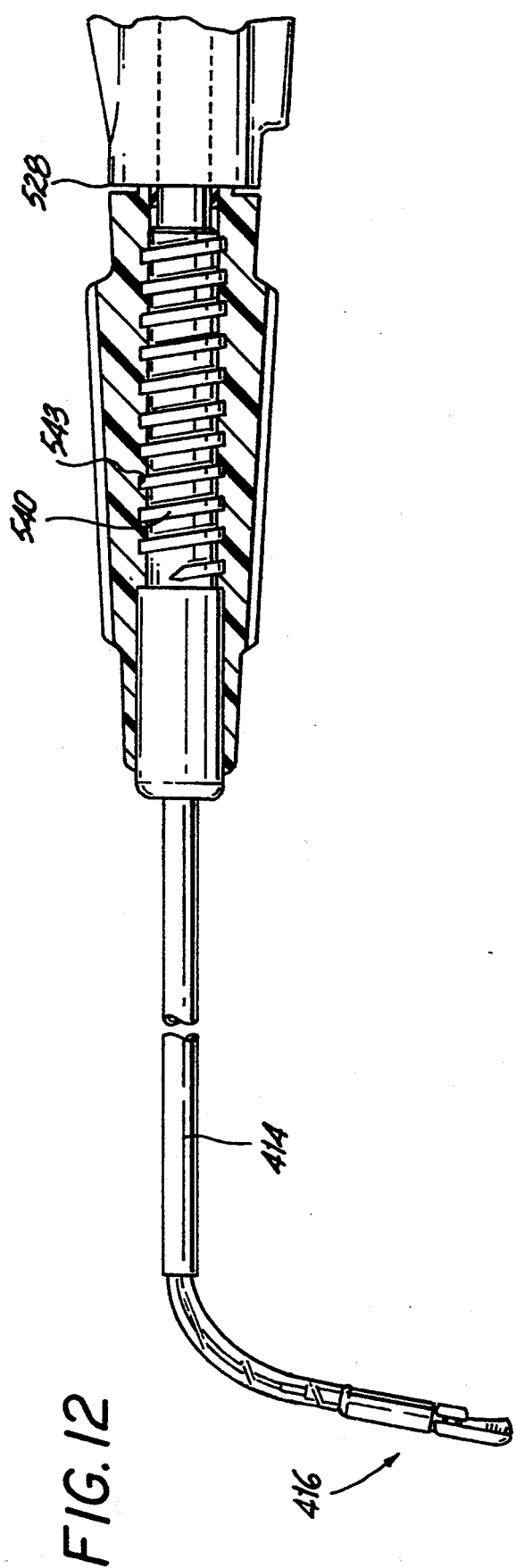
FIG. 13
FIG. 12

ARTICULATING ENDOSCOPIC SURGICAL APPARATUS

BACKGROUND OF THE INVENTION

This is a continuation-in-part of U.S. Ser. No. 07/872,057, filed Apr. 23, 1992, which is hereby incorporated by reference herein in its entirety.

FIELD OF THE INVENTION

The subject invention relates to surgical apparatus for performing laparoscopic and endoscopic surgical procedures, and more particularly to apparatus having a resilient end portion which can be articulated in a patient's body during a surgical procedure.

DESCRIPTION OF RELATED ART

In laparoscopic and endoscopic surgical procedures a small incision or puncture is made in the patient's body to provide access for a tube or a cannula device. Once extended into the patient's body, the cannula allows insertion of various surgical instruments such as scissors, dissectors or retractors to perform the surgery.

An example of an endoscopic surgical instrument is illustrated in U.S. Pat. No. 2,113,246 which issued to Wappler on Apr. 5, 1938. This patent discloses endoscopic forceps comprising an elongated conduit with jaws at the distal end thereof, a control rod in the conduit for controlling the operation of the jaws, and a control handle at the proximal end of the conduit which is operatively connected to the control rod. This surgical instrument is extremely limited in its application in that the angle of the conduit portion mounting the jaws cannot be adjusted in relation to the remaining portion of the conduit during a surgical procedure.

Improvements have been made in the art of surgical instruments to increase their range of operability. For example, U.S. Pat. No. 4,763,669 which issued to Jaeger on Aug. 16, 1988 discloses a microsurgery instrument with an adjustable angle of operation for obtaining cervical biopsies.

Similarly, U.S. Pat. No. 4,880,015 which issued to Nierman on Nov. 14, 1989 discloses a surgical device having an increased range of operability. In particular, this patent shows a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle to the distal end to the shaft for controlling the angular rotation of the distal portion of the instrument.

Of the references discussed above, none disclose a laparoscopic instrument for insertion into a body cavity through a cannula and adapted for a wide range of laparoscopic surgical applications. Further, these instruments are not provided with means for rotating the tool head about the longitudinal axis of the endoscopic portion of the instrument. Instead, a surgeon using either of these prior art instruments must physically rotate the entire instrument in order to change the rotational orientation of the distal end of the conduit or tube.

Shape memory alloys, such as those disclosed in U.S. Pat. No. 4,665,906 which issued to Jervis on May 19, 1987, have been employed to increase the range of operability of various medical instruments. For example, U.S. Pat. No. 3,620,212 which issued to Fannon et al. discloses an intrauterine contraceptive device formed of shape memory alloy, and U.S. Pat. No. 3,890,977 which issued to Wilson discloses a bendable catheter or cannula formed of shape memory alloy. These alloys may be deformed by an applied stress and then return toward an original unstressed shape or configuration when the stress is released.

In accordance with this principle, it has been found that the range of operability of an endoscopic surgical instrument, and in particular an articulating endoscopic surgical instrument may be greatly increased by forming the distal end of the endoscopic portion from a shape memory alloy.

Therefore, it is an object of the subject invention to provide an endoscopic surgical instrument having an articulating distal end which is formed from a shape memory alloy having elastic-like qualities.

It is another object of the subject invention to provide an endoscopic surgical instrument having a tool head which is independently moveable about two axes of rotation relative to the handle while the instrument is in use.

It is yet another object of the subject invention to provide a lightweight articulating endoscopic surgical instrument which provides a clearer line of sight for a surgeon during a surgical procedure.

It is still another object of the subject invention to provide an articulating endoscopic instrument in which a variety of different tool heads may be employed.

Another object of the subject invention to provide an articulating endoscopic instrument which may be used to perform electrocauterization during surgical procedures.

These and other objects of the subject invention will be made more apparent from the following description taken in conjunction with the accompanying drawings.

SUMMARY OF THE INVENTION

An endoscopic surgical instrument is disclosed for use in a wide variety of roles including electrocautery applications, cutting, grasping, dissecting or clamping during surgical procedures performed within a patient's body and particularly within the abdominal cavity.

The surgical instrument of the subject invention comprises a handle portion and an elongated endoscopic portion. The endoscopic portion includes an elongated fixed inner tubular section which depends from the handle portion, and an elongated outer tubular section which is mounted for coaxial reciprocating movement with respect to the fixed inner tubular section. An articulating member, which is preferably formed of a shape memory alloy, extends from the fixed inner tubular section and is movable in response to reciprocating movements of the outer tubular section. More particularly, the articulating member is movable between a first, unstressed position wherein a distal portion thereof is disposed at an angle to the longitudinal axis of the cylindrical portion and a second, stressed position wherein a distal portion thereof is substantially coaxial with the cylindrical portion of the instrument. Tool means are operatively connected to the distal end of the articulating member.

In a preferred embodiment of the subject invention, the surgical instrument may include a handle portion having a fixed handle and a pivoting handle. A connecting means, e.g., a cable or a cable/rod combination, extends from the pivoting handle through the endoscopic portion to the tool means. In this embodiment, the tool means may comprise a pair of cooperating jaws, the movement of which is controlled by operating the pivoting handle.

Preferred embodiments of the subject invention may also include means for rotating the endoscopic portion of the surgical instrument about the longitudinal axis thereof with respect to the handle portion. In this instance, an annular bushing, which may be concentrically disposed within an annular cuff, would be provided in the handle portion of the instrument. The proximal end of a section of the endoscopic portion of the instrument would be arranged within the bushing and would be rotatable about its longitudinal axis by rotating the annular cuff. An electrical connector may also be provided in the handle portion and would be in electrical contact with the tool means for establishing a means of cauterizing tissue at a surgical site.

In an alternate embodiment of the subject invention, the handle portion can include linkage means for reciprocating the outer tubular section of the cylindrical portion with respect to the inner tubular section, between a first position in which the resilient articulating member is in an unstressed condition and a second position wherein the resilient articulating member is in at least a partially stressed condition.

An alternate embodiment of the subject invention may also be provided with a quick-release mechanism for rapidly opening a pair of cooperating jaws. In this instance, the handle portion would include an elongated barrel portion, a pivoting handle connected to the barrel portion, and a fixed handle depending from the barrel portion. An elongated endoscopic section having opposed proximal and distal ends would depend from the barrel portion and a pair of cooperating jaws would depend from the distal end of the endoscopic portion. The quick-release mechanism would include rod means associated with the endoscopic section for operatively connecting the cooperating jaws and the pivoting handle. The rod means would be movable in an axial direction with respect to the endoscopic section, in response to movements of the pivoting handle, between a proximal position wherein the cooperating jaws are closed and a distal position wherein the cooperating jaws are open. The mechanism would further include self-locking clutch means disposed in the barrel portion for releasably maintaining the rod means in a predetermined position by exerting an actuating force on the rod means acting perpendicular to the axis thereof. Trigger means would be associated with the barrel portion for selectively releasing the clutch means from a predetermined position.

In yet another alternative embodiment of the subject invention, an axial drive screw assembly is operatively associated with the handle portion to effect longitudinal translation of the outer tubular section. The axial drive screw assembly includes a manipulator barrel threadingly engaged about an axially movable driving screw. The driving screw is connected at the distal end portion thereof to the elongated outer tubular section such that rotation of the barrel will cause corresponding longitudinal translation of the outer tubular section in the proximal direction to allow articulation of the tool assembly between a first substantially coaxial position and a second angularly disposed position. The subject invention may further include electrical insulation being provided intermediate the inner tubular section and the outer tubular section. Additionally, electrical insulation may be provided along the outer surfaces of the articulating member, the tool means and/or the outer tubular section. Electrical insulation is provided to prevent or inhibit, inter alia, current leakage, direct electrical contact between the inner and outer tubular sections, and the substantial transfer of thermal energy to the surgeon during an electrocauterization procedure.

Further features of the subject invention will become more readily apparent from the following detailed description of the invention taken in conjunction with accompanying drawings.

BRIEF DESCRIPTION OF THE DRAWINGS

Preferred embodiments of the subject invention will be described herein below with reference to the drawings, wherein:

FIG. 12 is a side elevational view in partial cross-section of the endoscopic portion and the tool assembly of the apparatus of FIG. 9 illustrating the articulating member in an unstressed position.

FIG. 13 is a side elevational view in partial cross-section of the endoscopic portion and the tool assembly of the apparatus of FIG. 9 illustrating the articulating member in a stressed position.

DETAILED DESCRIPTION OF THE PREFERRED EMBODIMENT

Figure 1:
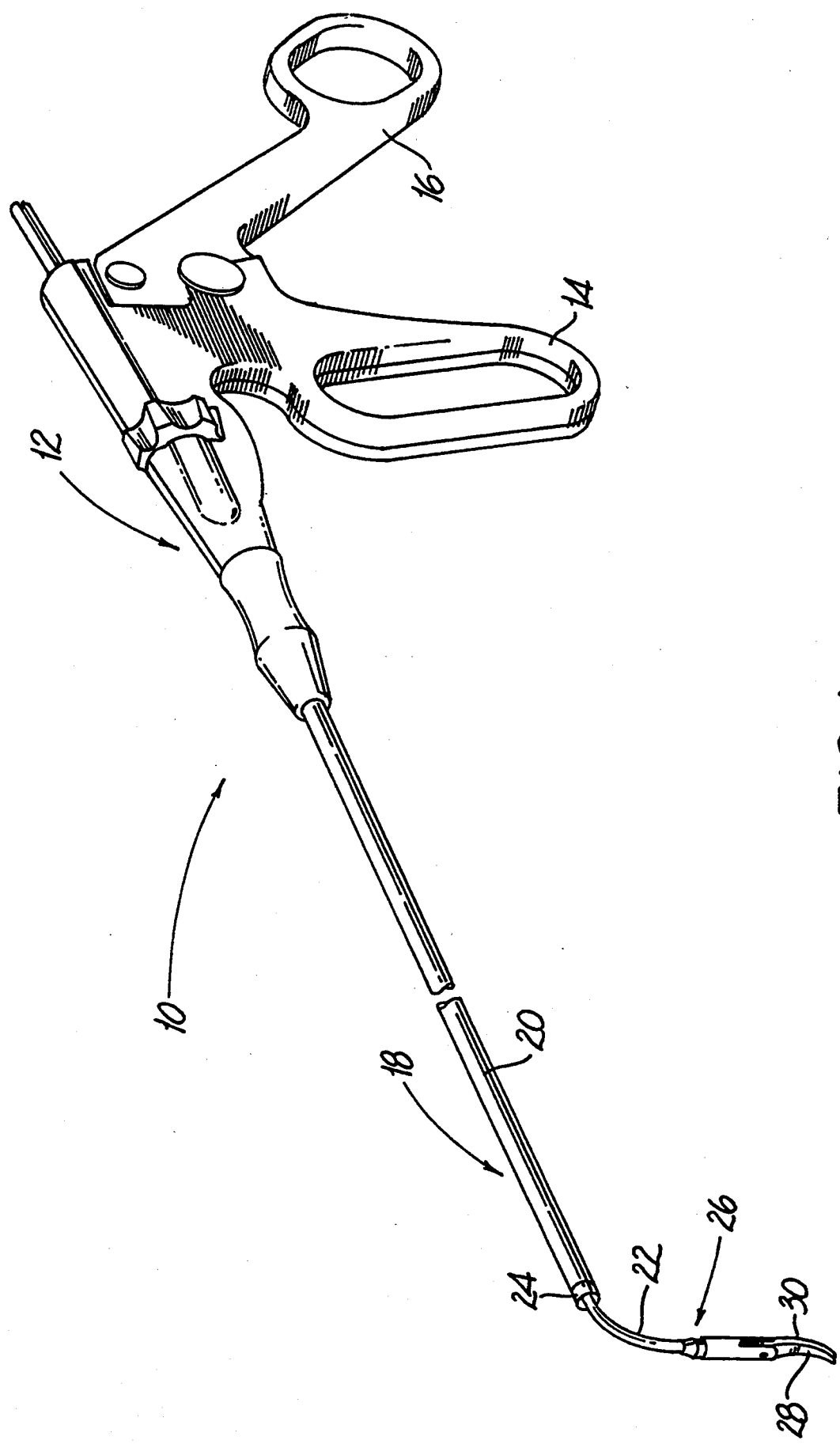
FIG. 1 is a perspective view of an articulating endoscopic surgical instrument in accordance with a preferred embodiment of the subject invention wherein the resilient articulating member is disposed in an unstressed position.

The articulating endoscopic surgical instrument of the subject invention is illustrated in FIG. 1 and is designated generally by reference numeral 10. Surgical instrument 10 comprises a handle portion 12 which includes a fixed handle 14 and a pivoting handle 16. An endoscopic portion 18 extends from handle portion 12 and includes an elongated cylindrical portion 20 and an articulating member 22. The articulating member 22 is extendable from the distal end 24 of cylindrical portion 20 and is preferably formed from a resilient material. A tool head 26 depends from articulating member 22 and includes cooperating jaws 28, 30. The cooperating jaws 28, 30 can be configured as graspers, dissectors, scissors, or clamps.

Figure 2:
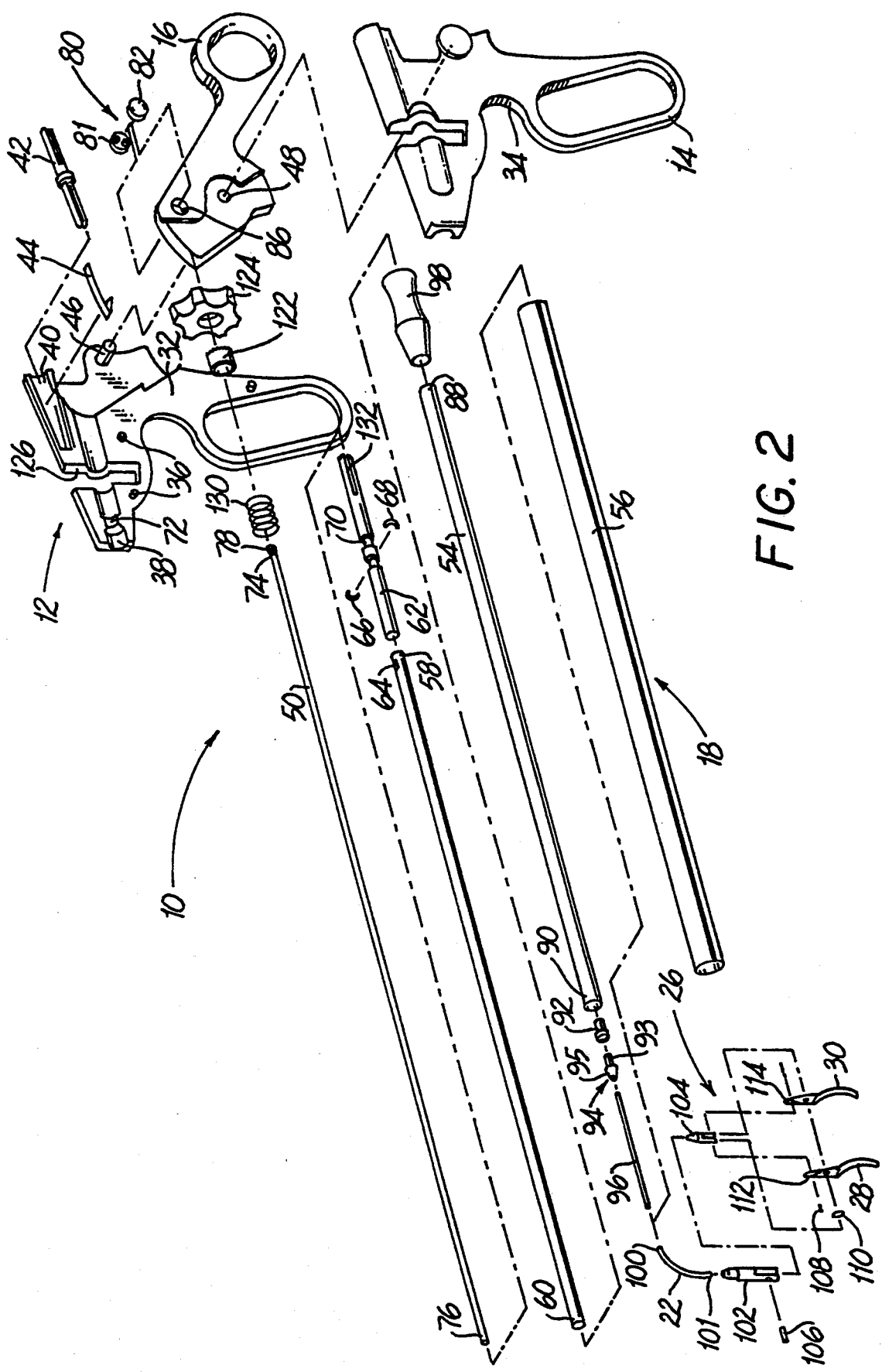
FIG. 2 is an exploded view of the articulating endoscopic surgical instrument of FIG. 1.
Figure 3:
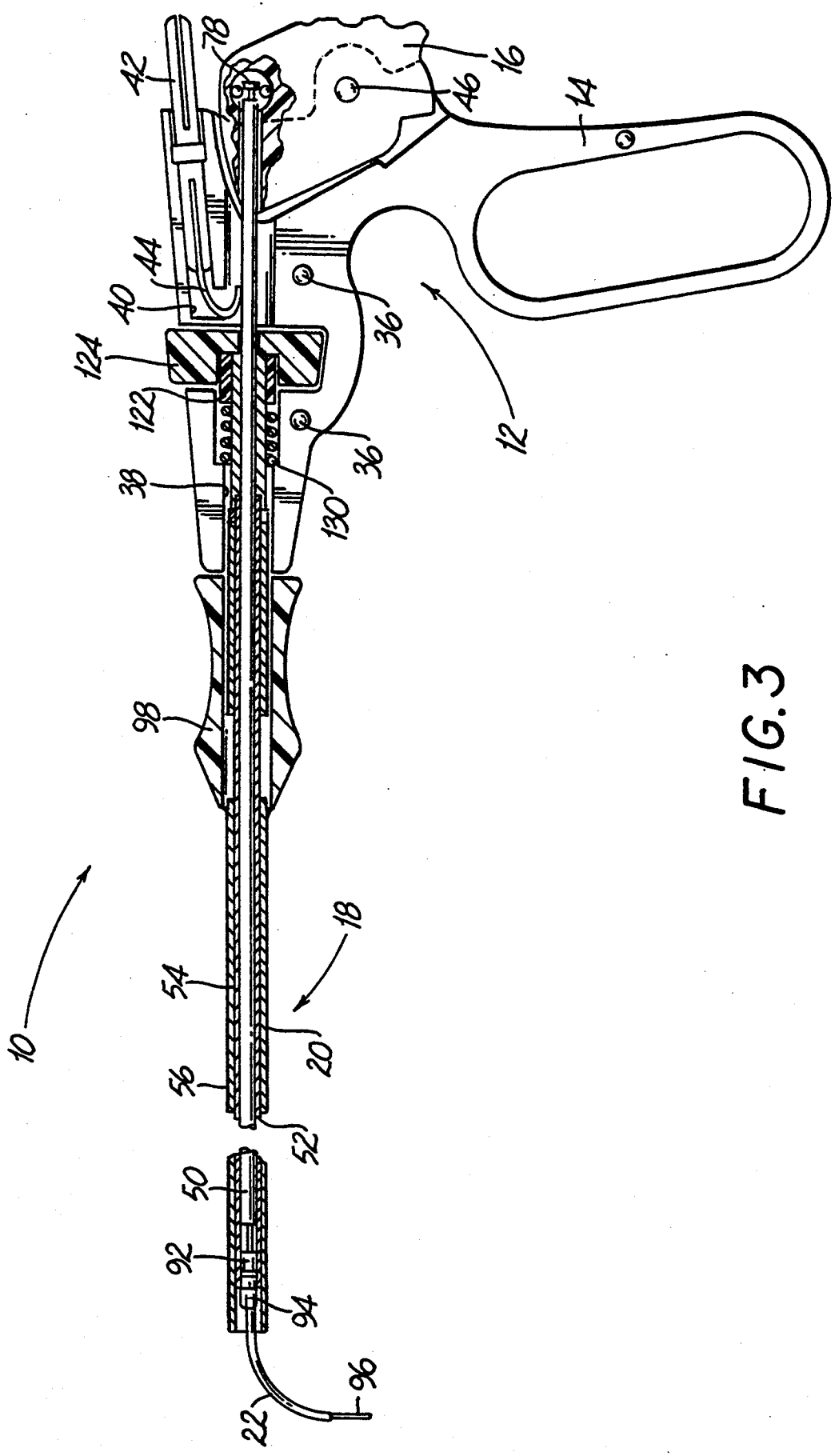
FIG. 3 is a side cross-sectional view of the articulating endoscopic surgical instrument of FIG. 1.

Referring to FIGS. 2 and 3, handle portion 12 and the fixed handle 14 associated therewith comprise opposed complementary sections 32, 34. Section 32 is provided with a plurality of bosses 36 for being mounted in a plurality of corresponding apertures (not shown) which are formed in section 34. A pivot pin 46 is formed on section 32 of handle portion 12 for extension through an aperture 48 provided in pivoting handle 16 for mounting the pivoting handle 16 to the handle portion 12. Each of the opposed sections 32, 34 are formed with a portion of a stepped bore 38 which is provided therein for accommodating various components of the subject invention, all of which will be described in greater detail hereinbelow.

Each of the opposed sections 32, 34 of handle portion 12 are also formed with a portion of a cavity 40 for maintaining a plug member 42. Plug member 42 is provided as a connection for use in electrocauterization procedures at the surgical site. A leaf spring 44 is disposed in handle portion 12 and is in electrical connection with the plug member 42 and cylindrical portion 18. In order to protect the surgeon who is using the device from electrical shock during cauterization procedures, the handle 202 is preferably constructed of a non-conducting material which renders the apparatus lightweight and electrically insulated.

The cylindrical portion 20 of the endoscopic portion 18 of the subject invention comprises a plurality of coaxial members including a center rod member 50, an inner tubular section 52, an outer tubular section 54, and a tubular cover section 56 consisting of shrink wrap. The shrink wrap cover section 56 forms an insulating layer over the cylindrical portion 20 for further protecting the surgeon and the patient from electrical shock during electrocauterization procedures.

The inner tubular section 52 has opposed proximal and distal ends 58 and 60, with the proximal end 58 thereof connected to an extension member 62. This connection is made by extending the proximal end 58 of the inner tubular section 52 into the extension member 62. This enables a notch 64, which is formed adjacent to the proximal end 58 thereof, to be engaged by a pair of opposed clips 66 and 68, which are fastened amid extension member 62. To mount extension member 62 within the stepped bore 38 of handle portion 12 a circumferential groove 70 is provided on extension member 62. Groove 70 is engaged by an annular flange 72 which is formed in the stepped bore 38.

Center rod member 50, which has opposed proximal and distal ends 74 and 76, extends through the inner tubular section 52 and extension member 62. A head 78 is formed on the proximal end 74 of rod member 50 and is engaged in a locking clip 80. Locking clip 80 comprises opposed complementary sections 82 and 84, and is disposed in a circular port 86 provided in pivoting handle 16. The center rod member 50 is movable in an axial direction in response to movements of the pivoting handle 16.

The outer tubular section 54 of cylindrical portion 20 has opposed proximal and distal ends 88 and 90 and is mounted for reciprocating coaxial movement with respect to the inner tubular section 52. A straightener 92 is disposed within the distal end 60 of inner tubular section 52. An adaptor 94 having a frusto-conical head 93 and a body 95 extends into the distal end 60 of inner tubular section 52 and is disposed adjacent the straightener 92. An elongated cable 96 extends through the adaptor 94 and the straightener 92 and is mounted to the center rod 50.

The articulating member 22 of endoscopic portion 18 is preferably formed of a resilient shape memory alloy, the configuration of which can be controlled mechanically by applying a stress to the material. In the present embodiment, the unstressed shape of the articulating member 22 is a 90° elbow. The provision of elbows configured at other unstressed angles is within the scope of the present invention and may be dictated by the needs of the surgeon. In contrast, when a stress is applied to articulating member 22, by movement of the outer tubular section 54 relative to the inner tubular section 52, the articulating member 22 will translate to a substantially elongated position.

The articulating member 22, which is preferably of tubular configuration, includes opposed proximal and distal ends 100 and 101, with the proximal end 100 thereof being connected to the frusto-conical head 93 of the adaptor 94. Cable 96 which depends from rod member 50 extends through articulating member 22 to a clevis 102. Clevis 102 is operatively connected to the distal end 101 of articulating member 22. A piston 104 is arranged in clevis member 102 and is operatively connected to the distal end of cable 96. The cooperating jaws 28, 30 are pivotably mounted within clevis 102 by a pivot pin 106, and are also mounted to piston 104 by a pin 108. More particularly, pin 108 extends through a washer 110 and camming slots 112 and 114 which are respectively formed in the cooperating jaws 28, 30.

A slider knob 98 is fixedly mounted to the proximal end 88 of outer tubular section 54. Slider knob 98 is adapted to be gripped by a surgeon and slidably manipulated so as to cause the outer tubular section 54 to reciprocate in an axial direction with respect to the fixed inner tubular section 52 of cylindrical portion 20 for moving the articulating member 22.

The endoscopic surgical instrument 10 of the subject invention further comprises a mechanism for rotating the articulating endoscopic member 22 of endoscopic section 18 about the longitudinal axis of cylindrical portion 20, relative to the handle portion 12. This mechanism comprises an annular bushing 122 which is concentrically mounted within a rotatable collar 124. Collar 124 is mounted within a port 126 formed in the stepped bore 38 of handle portion 12. Bushing 122 is maintained against collar 124 by a coiled spring 130 disposed in a section of bore 38. Spring 130 acts to bias bushing 122 toward the proximal end of bore 38. The proximal end of extension member 62 is formed with a longitudinal slot 132 which is mountable in bushing 122 so as to facilitate rotation of the articulating member 22 with respect to the handle portion 12 by rotating collar 124.

Figure 4:
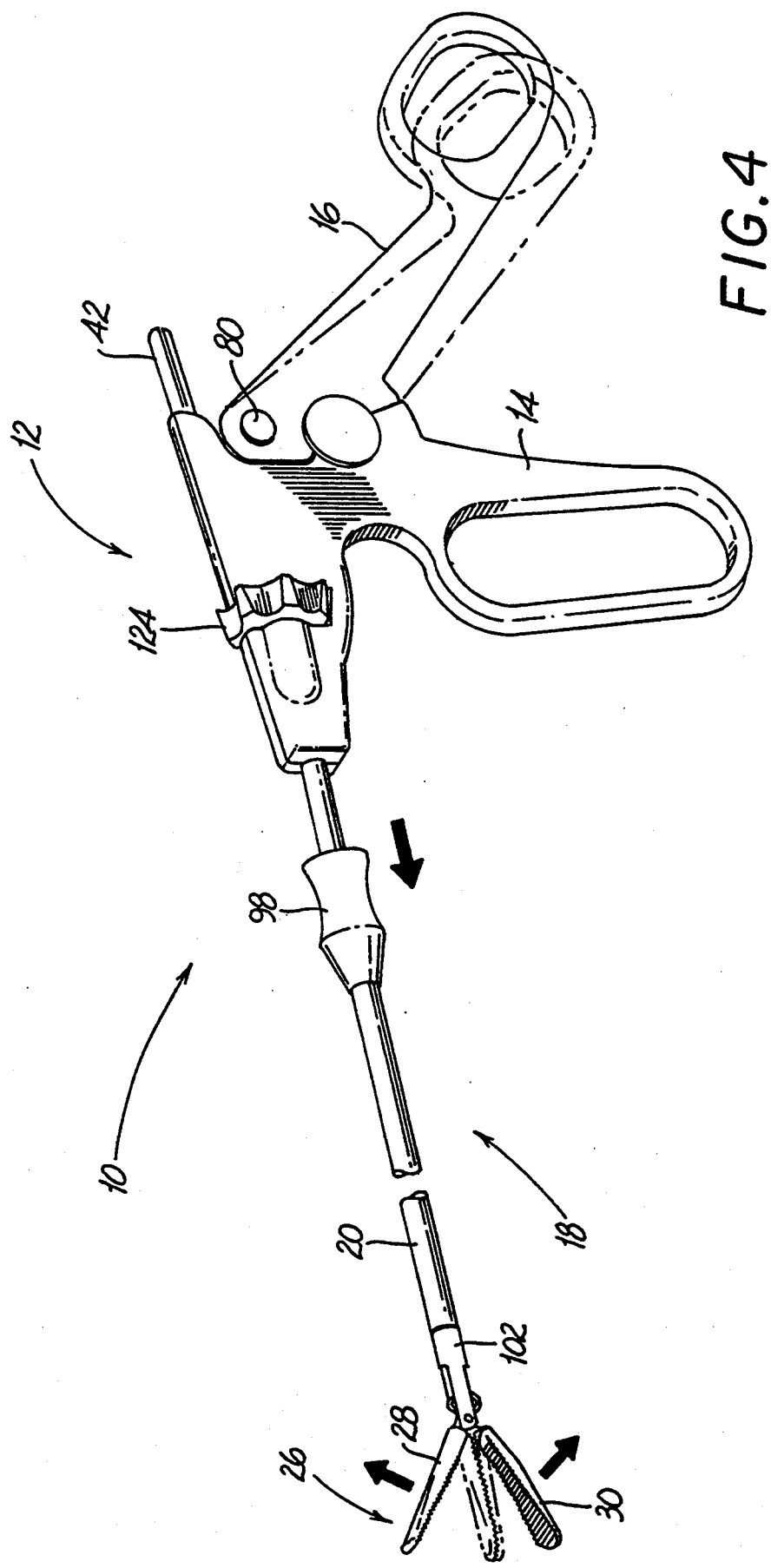
FIG. 4 is a perspective view of the articulating endoscopic surgical instrument of FIG. 1 wherein the resilient articulating member is disposed in a stressed position.
Figure 5:
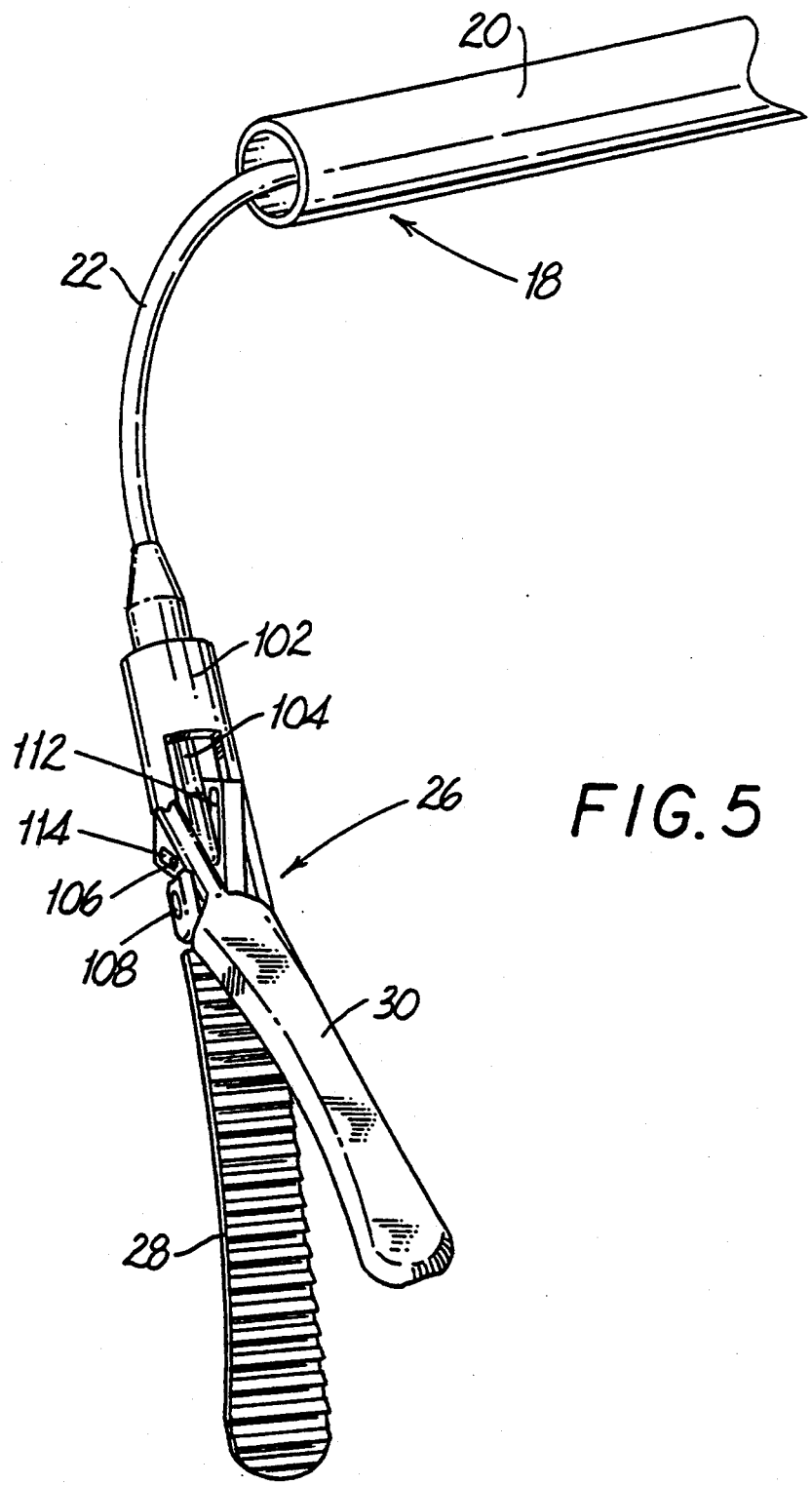
FIG. 5 is an enlarged perspective view of the articulating endoscopic portion of the surgical instrument of FIG. 1, illustrating a pair of cooperating jaws configured as a grasper.

Referring to FIGS. 4 and 5, the operation of the cooperating jaws 28, 30 of tool head 26 is accomplished by moving the pivoting handle 16. The movement of pivoting handle 16 causes the head 78 of center rod 50 to translate axially, causing cable 96 and piston 104 to move. To close the cooperating jaws 28 and 30, which are normally open, the pivoting handle 16 is squeezed by the surgeon, causing center rod 50 to pull cable 96 in a proximal direction. The movement of cable 96 causes a corresponding axial movement of piston 104 in clevis 102. The movement of piston 104 causes pin 108 to cam proximally within slots 112 and 114 of jaws 28, 30 respectively, causing cooperating jaws 28, 30 to close.

The movement of the resilient articulating member 22 of endoscopic portion 18 is accomplished by moving the outer tubular section 54 relative to the inner tubular section 52. More particularly, to move the articulating member 22 from an unstressed position, as best seen in FIG. 5, wherein it is substantially orthogonal to the cylindrical portion 20, the outer tubular section 54 is slid in a distal direction with respect to the handle portion 12. As outer tubular section 54 is gradually moved in this manner, a stress is gradually applied to articulating member 22. This application of stress causes the distal portion of articulating member 22 to move toward a position wherein it is substantially coaxial with the inner tubular section 52 as best seen in FIG. 4. The cooperating jaws 28, 30 may be operated in any angular position of the articulating member 22.

Figure 6:
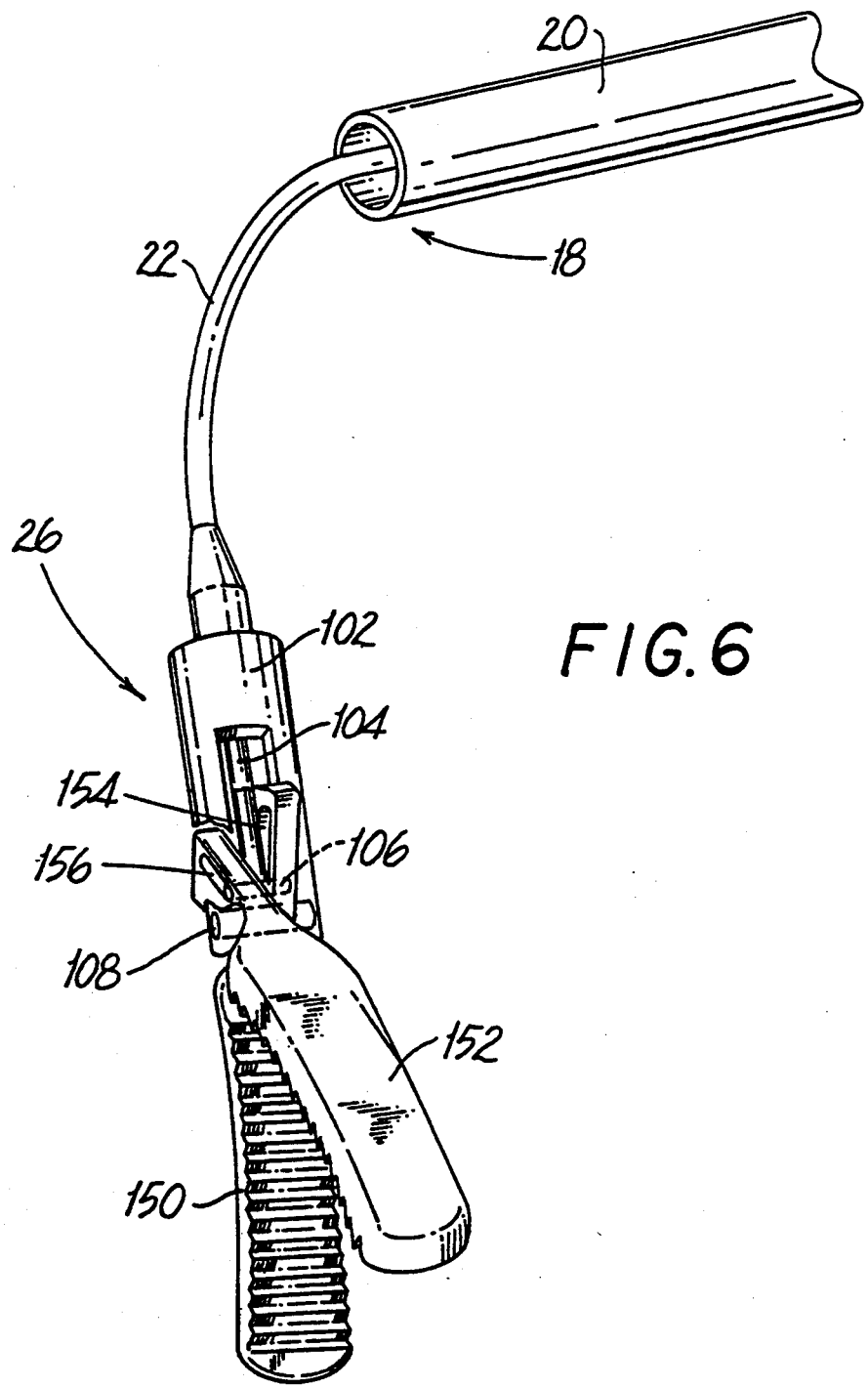
FIG. 6 is an enlarged perspective view of the articulating endoscopic portion of the surgical instrument of the subject invention of FIG. 1, illustrating a pair of cooperating jaws configured as a dissector.

Turning now to FIG. 6, an alternate embodiment of the tool head 26 of the articulating endoscopic surgical instrument 10 of the subject invention is illustrated. In this embodiment, the tool head 26 includes cooperating dissector jaws 150, 152 which are pivotably mounted by pin 108 to clevis 102 on the distal portion of the articulating member 22 of endoscopic portion 18. Dissector jaws 150, 152 are provided with camming slots 154, 156 respectively formed in the distal ends thereof. As in the preferred embodiment, camming pin 108 is accommodated within slots 154, 156 and slides in response to axial movements of piston member 104 within clevis 102 when the pivoting handle 16 is operated to open and close the cooperating jaws 150, 152.

Figure 7:
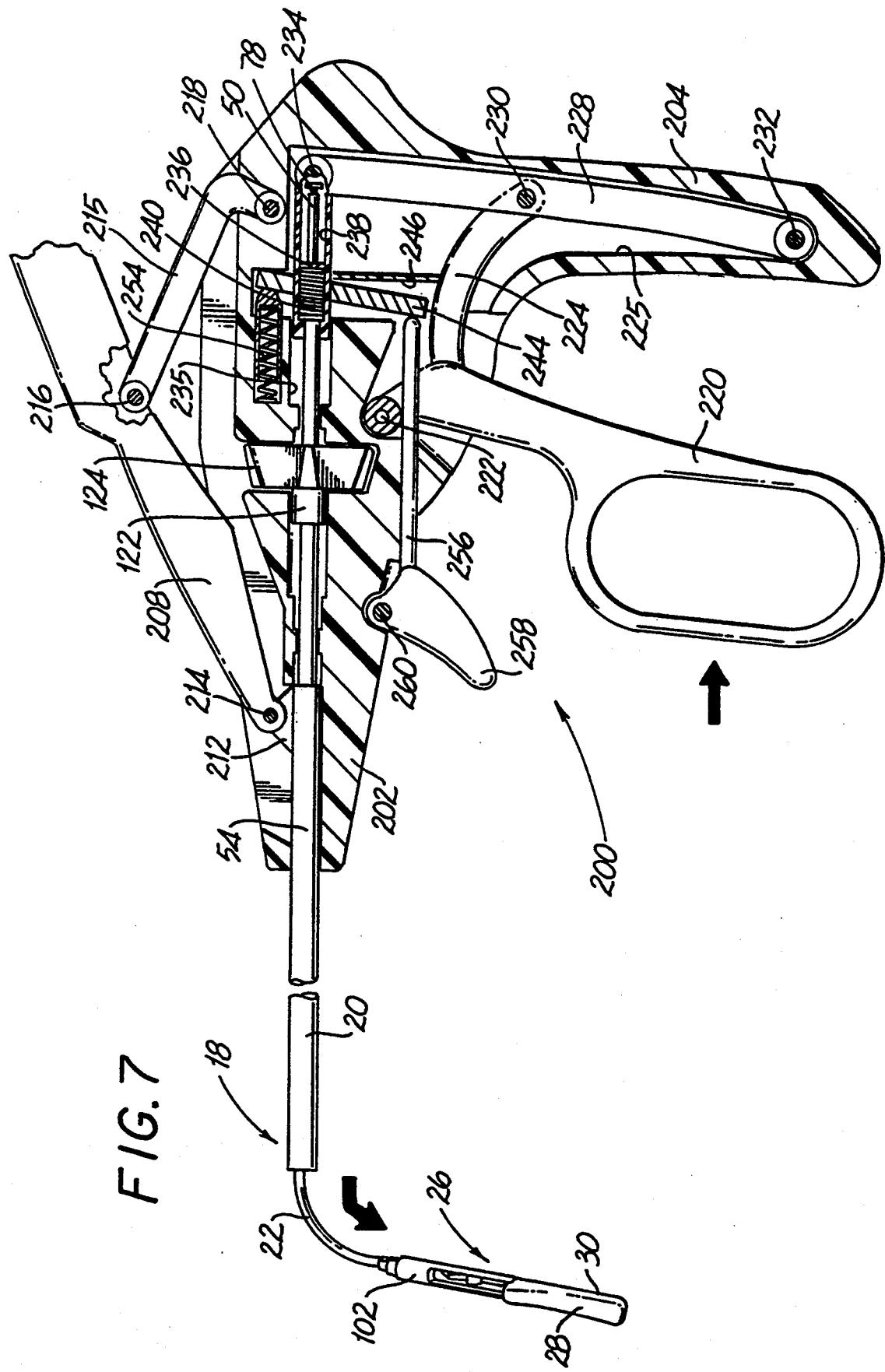
FIG. 7 is a side cross-sectional view of an alternate embodiment of the handle portion of the articulating endoscopic surgical instrument of the subject invention.
Figure 8:
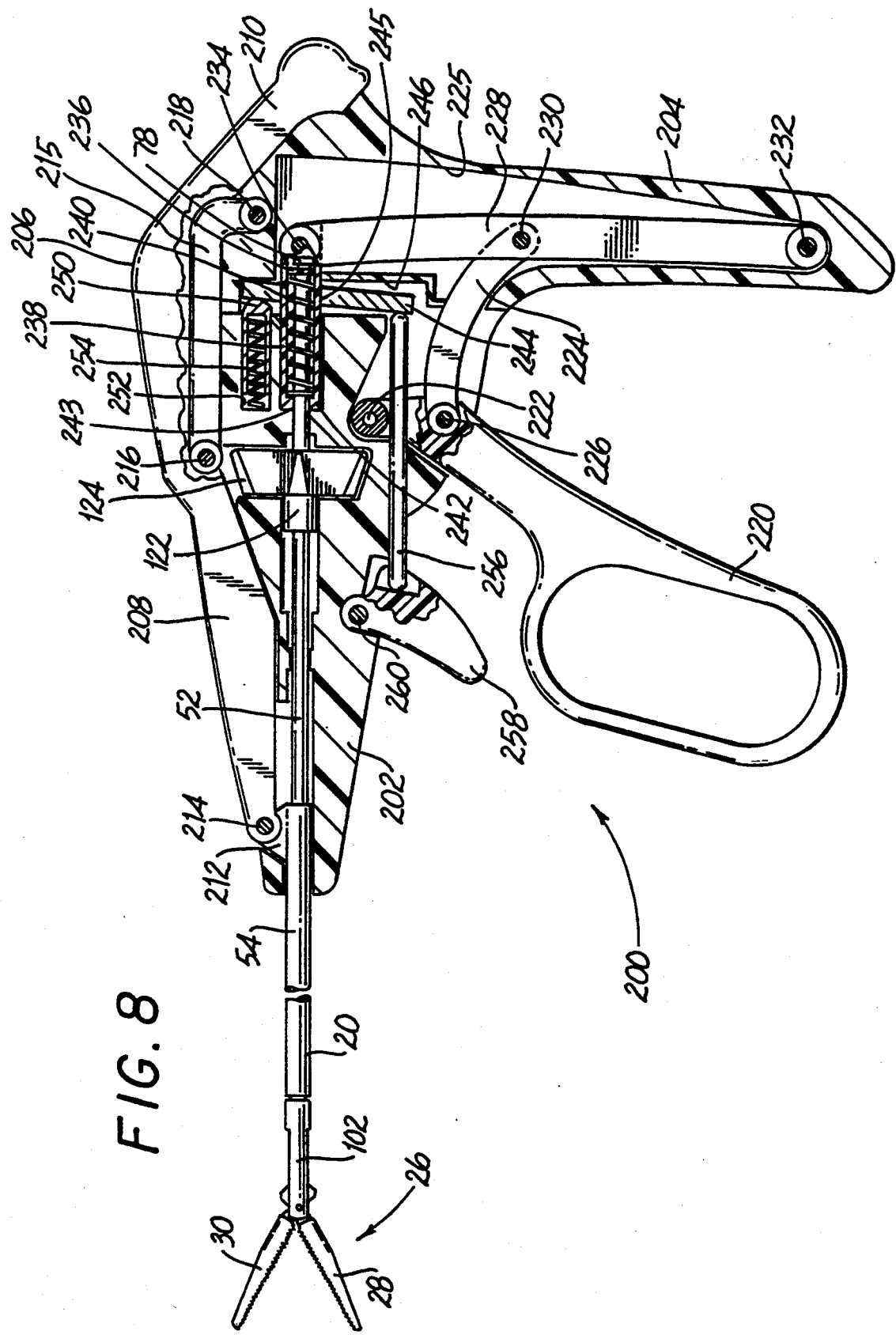
FIG. 8 is a side cross-sectional view of the handle portion of FIG. 7, in a position corresponding to the cooperating jaws being opened.

Turning now to FIGS. 7 and 8, an alternate embodiment of a handle assembly of the endoscopic surgical instrument of the subject invention is illustrated and is designated generally by reference numeral 200. Handle assembly 200 has a barrel portion 202 and a handle portion 204 which depends orthogonally from the barrel portion 202. A linkage mechanism is associated with handle assembly 200 for achieving the reciprocating coaxial movements of the outer tubular section 54 relative to the inner tubular section 52. This mechanism includes a generally L-shaped crank member 206 having an elongated body 208 and a leg 210. The body portion 206 is pivotably mounted to a cuff member 212 by a pin 214. Cuff member 212 is fixedly mounted to the proximal end of the outer tubular section 54. The body 208 is also connected to an L-shaped link 215 at a pivot point 216, intermediate the length thereof. Link 215 is mounted to the barrel portion 202 of handle assembly 200 by pivot pin 218.

To move the articulating member 22 of endoscopic portion 18 from an unstressed position to a stressed position by employing the linkage mechanism, the crank member 206 is pivoted toward the barrel portion 202 of handle assembly 200. This pivotal movement causes cuff member 212 to advance in a distal direction, thereby causing the outer tubular section 54 to translate distally relative to inner tubular section 52 thus applying a stress to articulating member 22.

The handle assembly 200 further includes a unique quick-release, self-locking clutch mechanism, for operating the cooperating jaws 28, 30 which are arranged on the distal end of articulating member 22. The clutch mechanism includes a pivoting handle 220 mounted to the barrel portion 202 by a pivot pin 222. The pivoting handle 220 is connected to an arcuate link 224 by a pivot pin 226. Arcuate link 224 is connected to an elongated link 228 at a pivot pin 230 which is disposed intermediate the length thereof. The bottom end of link 228 is pivotably mounted to the bottom of handle portion 204 by a pin 232. Elongated link 228 is mounted for pivotal movement within a cavity 225 which is formed within the handle portion 204 of handle assembly 200.

The proximal head 78 of center rod 50 is secured in the top end 234 of elongated link 228. Therefore, center rod member 50 is movable in an axial direction in response to pivoting movements of pivoting handle 220. A carrier cylinder 238 is slidably maintained in a chamber 235 and is also connected to the top end 234 of elongated link 228. Carrier cylinder 238 is formed with a retaining wall 242 having a circular aperture 243 provided therein through which extends the inner tubular section 52 of cylindrical portion 20. An annular retainer ring 236 is mounted coaxially on inner tubular member 52 adjacent to the proximal head 78 of rod member 50, and is arranged within the carrier cylinder 238. A coiled spring 240 is disposed coaxially on inner tubular section 52, within the carrier cylinder 238, between retaining wall 242 and retaining ring 236, for biasing the top end 236 of pivoting link 228.

The quick-release self-locking clutch mechanism further includes a rocker disk 244 which is disposed in a cavity 242 provided in barrel portion 202 of handle assembly 200. A circular aperture 245 extends through rocker disk 244 for receiving the cylindrical carrier 238. Rocker disk 244 functions to releasably maintain the carrier cylinder 238 in a desired position by establishing frictional contact between corresponding points on the surface of aperture 245 and the circumference of the outer wall of carrier cylinder 238. This frictional contact is maintained by an actuating force which acts perpendicular to the axis of carrier cylinder 238. The actuating force is provided by a spring loaded plug 250 which is disposed in a cavity 252 in barrel portion 202. In particular, the plug 250 is biased towards the proximal end of the barrel portion 202 by a coiled spring 254 which exerts a biasing force on the upper portion of rocker disk 244. The biasing force acts parallel to the axis of the cylindrical carrier 238 and tilts the upper portion of rocker disk 244 toward the proximal end of barrel portion 202, thereby creating the actuating force which maintains frictional contact between carrier cylinder 238 and rocker disk 244. A trigger 258 is pivotably mounted to the barrel 202 by a pivot pin 260. A push rod 256 extends between the trigger 258 and the bottom portion of rocker disk 244. The trigger 258 may be depressed so as to cause push rod 256 to tilt rocker disk 244 out of its engaging position, overcoming the actuating force.

In use, the self-locking clutch mechanism of handle assembly 200 serves as a quick-release system for opening the cooperating jaw 28, 30 which depend from the articulating member 22 of endoscopic portion 18. To operate the clutch mechanism, the pivoting handle 220 is pulled toward the handle portion 204 of handle assembly 200. This pivoting movement causes curved link 224 to push the elongated link 228 toward the proximal wall of cavity 225. The movement of elongated link 228 pulls the proximal head 78 of center rod member 50 and the carrier cylinder 238 toward the proximal end of chamber 235 formed in barrel portion 202. As the center rod member 50 translates axially in a proximal direction, the piston 104 in clevis member 102 cams the cooperating jaws 28 and 30 closed. As the cylindrical carrier 238 translates axially in a proximal direction, spring 240 is caused to compress against the retainer ring 236. The carrier cylinder 238 is maintained in this "spring-loaded" position by the frictional contact between rocker disk 244 and the outer surface of carrier cylinder 238 caused by the actuating force acting perpendicular to the axis of carrier cylinder 238.

To open the cooperating jaws 28, 30, the trigger 258 is depressed so as to cause push rod 256 to urge rocker disk 244 out of contact with carrier cylinder 238. The coiled spring 240 decompresses against the retaining wall 242 of carrier cylinder 238, forcing it to advance distally in chamber 235. As carrier cylinder 238 moves distally, pivoting link 228 is also moved in a generally distal direction thereby relieving the tension on center rod member 50, and thus causing the cooperating jaws 28, 30 to cam to an open position.

Figure 9:
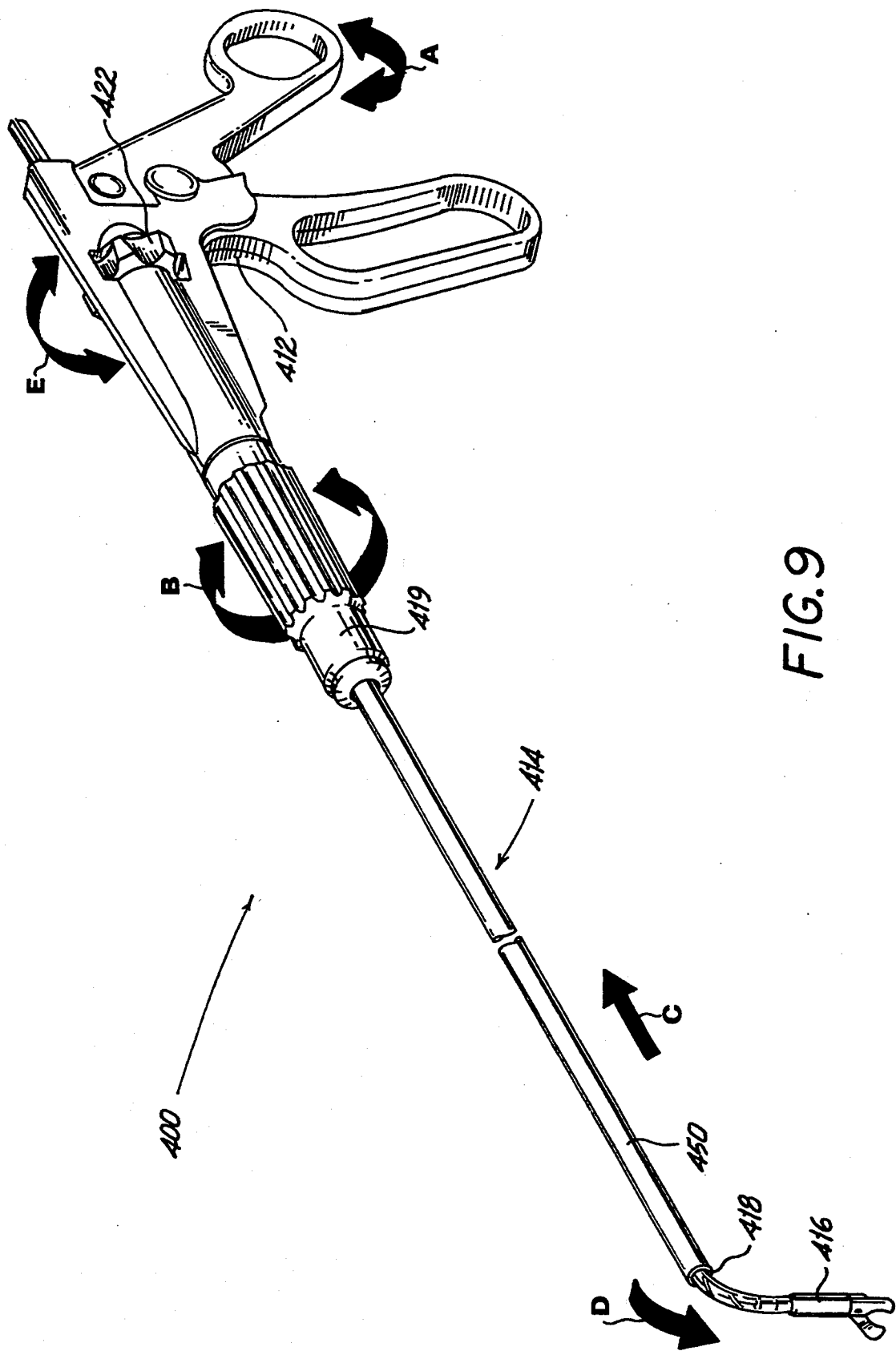
FIG. 9 is a perspective view of an articulating endoscopic surgical instrument in accordance with an alternative embodiment of the subject invention wherein the resilient articulating member is disposed in an unstressed position.

Yet another alternative embodiment of the endoscopic surgical instrument of the subject invention is illustrated in FIG. 9 and is designated generally by reference numeral 400. Briefly, the surgical instrument 400 comprises a handle assembly 412, an elongated tubular portion 414 extending longitudinally from the handle assembly 412 and preferably dimensioned for endoscopic utilization, and a tool assembly 416 operatively associated with the distal end 418 of the elongated body portion 414.

The surgical apparatus 400 of the subject invention is particularly adapted to provide the user with an increased range of operability to perform a surgical task while shielding the user from the thermal energy and current leakage which may be generated by or associated with the surgical apparatus 400 when the latter is used in an electrocauterization task. The increased range of operability of surgical apparatus 400 is achieved through a plurality of mechanisms, each functioning to move the tool assembly 416 of the instrument within a distinct rotational and/or angular plane of motion. One of the mechanisms effects movement of the tool assembly 416 into an angularly disposed position with respect to the longitudinal axis of the elongated body portion 414. This first mechanism includes an axial drive screw assembly 419 which causes translation of an outer tubular section 450. A second mechanism is provided for effectuating remote rotation of the tool assembly 416 about the longitudinal axis of the elongated body portion 414. This second mechanism comprises a rotatable collar 422 operatively associated with the handle assembly 412. Each of these mechanisms, which function to increase the range of operability of the surgical apparatus 400, will be discussed in greater detail hereinbelow.

Figure 10:
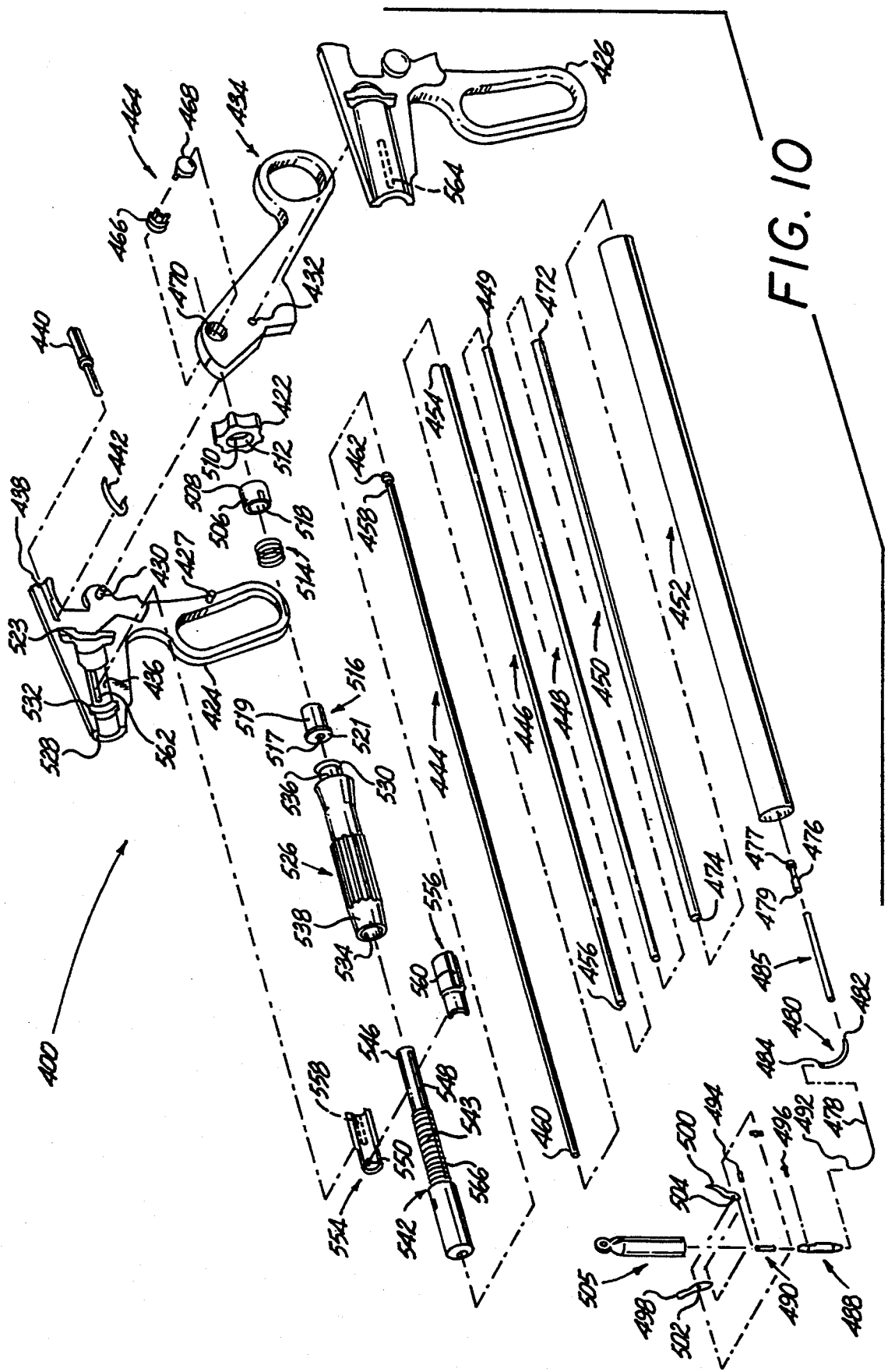
FIG. 10 is an exploded perspective view of the articulating endoscopic surgical instrument of FIG. 9.
Figure 11:
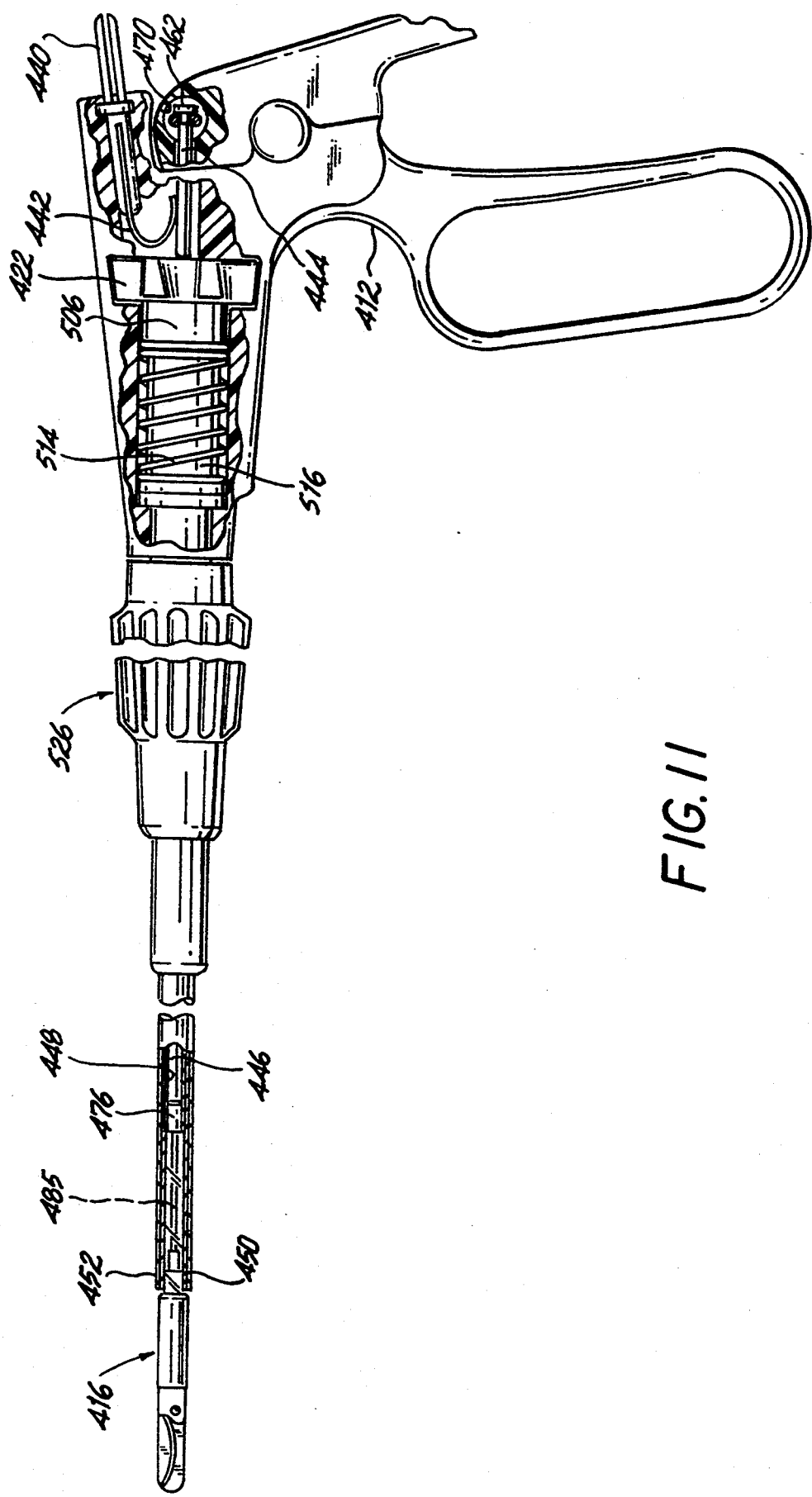
FIG. 11 is a side cross-sectional view of the articulating endoscopic surgical instrument of FIG. 9.

Turning to FIGS. 10 and 11, the handle assembly 412 of the surgical invention comprises opposed complementary sections 424 and 426. Section 424 is provided with at least one boss 427 mounted in a corresponding aperture (not shown) formed in section 426. A pivot pin 430 is formed on section 424 of the handle assembly 412 for extension through an aperture 432 provided in pivoting handle 434 for enabling the mounting of pivoting handle 434 to the handle assembly 412. Each of the opposed sections 424, 426 are formed with a portion of a bore 436 respectively provided therein for accommodating various components of the surgical apparatus 400 of the subject invention.

Each of the opposed sections 424 and 426 of the handle assembly 412 are additionally formed with a portion of a cavity 438 for maintaining a plug member 440. Plug member 440 is provided therein to enable electrical connection between the surgical apparatus 400 and an appropriate medical power supply (not shown) for enabling electrocauterization at a surgical site. A leaf spring 442 is disposed in handle assembly 412 and is in electrical association with the plug member 440. In order to protect the surgeon who is using the surgical apparatus 400 from current leakage and thermal energy which may be associated with electrocauterization procedures, opposing handle sections 424 and 426 along with the pivoting handle 434 are preferably constructed of a non-conducting material which renders the apparatus lightweight and electrically insulated.

Referring now to FIG. 10, opposing complementary handle sections 424 and 426 may be mounted to one another such that at least one boss 427 provided on section 424 engages with at least one corresponding aperture 428 (not shown) provided on section 426. It is also to be appreciated that opposing complementary handle sections 424 and 426 may be mounted to one another through any known means of affixation including, for example, sonic welding or gluing. Once assembled, the handle assembly 412 defines a bore portion 436, a fixed gripping handle 443, and a pivoting handle member 434. Pivoting handle 434 is mounted adjacent the bore portion 436 by the pivot pin 430.

The elongated cylindrical portion 414 of the surgical apparatus 400 of the subject invention comprises a plurality of coaxial members including a center rod member 444, an inner tubular section 446, an inner electrically insulating tubular section 448, an outer tubular section 450, and an outer tubular cover section 452 consisting of shrink wrap. In particular, the inner insulating tubular section 448 functions to provide an electrical insulation barrier being peripherally disposed between the inner tubular section 446 and the outer tubular section 450. The inner insulating tubular section 448 is preferably constructed of a suitable electrically insulating material which provides optimal electrical insulation between the inner tubular section 446 and the outer tubular section 450 during an electrocauterization procedure. Additionally, the shrink wrap cover section 452 provides an electrical insulating layer peripherally along the outer surface of the outer tubular section 450 for further protecting the surgeon and patient from current leakage which may occur during a electrocauterization procedure.

The inner tubular section 446 has opposed proximal and distal ends 454 and 456, with the proximal end 454 being operatively associated with the rotatable collar 422 in the handle assembly 412. Further, the proximal end 454 of the inner tubular section 446 is electrically associated with the leaf spring 442 in the handle assembly 412. In particular, as shown in FIG. 11, the inner tubular section 446 extends through the inner insulating tubular section 448 such that the inner insulating tubular section 448 is disposed intermediate the proximal and distal ends 454 and 456 of the inner tubular section 446.

Center rod member 444, which has opposed proximal and distal ends 458 and 460, extends through the inner tubular section 446. A head 462 is formed on the proximal end 458 of the center rod member 444 and is engaged in a locking clip 464. Locking clip 464 comprises opposed complimentary sections 466 and 468, and is disposed in a circular port 470 provided in pivoting handle 434. The center rod member 444 is movable in an axial direction in response to movements of the pivoting handle 434.

The outer tubular section 450 of cylindrical portion 414 has opposed proximal and distal ends 472 and 474 and is mounted for reciprocating coaxial movement with respect to the inner tubular section 446. An adapter 476 includes opposed proximal and distal ends 477 and 479, and is disposed within and electrically associated with the distal end 456 of the inner tubular section 446, such that the proximal end 477 of the adaptor 476 engages with the distal end 456 of inner tubular section 446. An elongated cable 478 extends through the adaptor 476 and is operatively connected to and electrically associated with the center rod 444.

The articulating member 480 of surgical apparatus 400 is preferably formed of a resilient shape memory or superelastic alloy, the configuration of which can be controlled mechanically by applying a stress to the material. In the present embodiment, the unstressed shape of the articulating member 480 is a 90° elbow. The provision of elbows configured at other unstressed angles is within the scope of the present invention and may be dictated by the needs of the surgeon. In contrast, when a stress is applied to articulating member 480, by movement of the outer tubular section 450 relative to the inner tubular section 446, the articulating member 480 will translate to a substantially linear, elongated position.

The articulating member 480, which is preferably of tubular configuration, includes opposed proximal and distal ends 482 and 484, with the proximal end 482 thereof being connected to the distal end 479 of the adaptor 476. The cable 478 depends from center rod member 444 and extends through articulating member 480 and clevis 488. Cable 478 is electrically and operatively associated with clevis 488. Clevis 488 is operatively connected to the distal end 484 of the articulating member 480. A piston 490 is arranged in clevis member 488 and is operatively and electrically connected to the distal end 492 of cable 478. Cooperating jaws 498, 500 are pivotably mounted within clevis 488 by a pivot pin 496, and are also mounted to piston 490 by a pin 494. More particularly, pin 494 extends through a washer 499 and camming slots 502 and 504 which are respectively formed in cooperating jaws 498, 500. Additionally, an electrically insulating tubular cover 485 may be provided at the distal end 418 of the elongated body portion 414 to further prevent current leakage to the patient and/or user during an electrocauterization procedure. Insulating tubular cover 485 further provides a low friction bearing surface, thereby minimizing the force required to articulate member 480 which also provides a smooth transition between clevis 488 and adapter 476. In particular, the articulating member 480 extends through the electrically insulating tubular cover 485, wherein the proximal end 487 of the tubular 485 is associated with the adaptor 476 while the distal end 489 is associated with clevis 488. A cap 505 is typically provided to cover the jaws 488, 500 for disposal.

In a preferred embodiment, pivot pin 496 is electrically isolated from the electrocautery current which passes from cable 478, through clevis 488, to jaws 498, 500. This may be accomplished by including electrically insulating bushings on either side of pivot pin 496 and/or by fabricating pivot pin 496 from a dielectric material, e.g., a ceramic or plastic.

The mechanism for effectuating rotation of the tool assembly 416, including jaw members 498 and 500, and the clevis portion 488 which houses and/or supports the jaw member 498 and 500, comprises a rotatable collar 422, and a rotator assembly associated with the bore portion 436 of handle assembly 412. The rotator assembly includes a ratchet bushing 506 having a plurality of rearwardly projecting ratchet teeth 508 configured for ratcheting interaction with corresponding forwardly extending ratchet teeth 510 defined on an inner race surface 512 of rotatable collar 422. A helical compression biasing spring 514, which is positioned proximal to a spring retention ring 516 effectively urges ratchet bushing 506 into operative contact with the inner race 512 of rotatable collar 422 to interengage the respective ratchet teeth 508, 510. The spring retention ring 516 is mounted for rotational movement within the handle assembly 412 which is achieved through an annular flange 521 retained in a corresponding dimensioned annular chamber 523 formed in the bore portion 436. An axial passage 518 extends through ratchet bushing 506 wherein the inner tubular section 446 slidably receives therethrough enabling the inner tubular section 446 to be operatively associated with the rotatable collar 422. Inner tubular section 446 extends operatively from the bore portion 436 of the handle assembly 412 through the elongated tubular cylindrical portion 414 of the surgical apparatus 400 to the tool assembly 416 being associated with the distal end 456 thereof. Additionally, the spring retention ring 516 is provided with an axial passageway 517 wherein the inner insulating tubular member 448 extends therethrough, with the proximal end 449 of insulating tubular member 448 being engagably retained in the axial passageway 517 by a lance connection 519. In use, axial rotation of rotatable collar 422 will cause corresponding rotation of inner tubular section 446 to effectuate remote rotation of the tool assembly 416 about the longitudinal axis defined by the elongated body portion 414 of surgical apparatus 400.

The mechanism for effectuating the articulation of the tool assembly 416 within an angular sector of rotation, preferably extending through about 0°-90° and more preferably through about 0°-80° from the longitudinal axis includes an axial drive screw assembly 419 which includes an elongated manipulator barrel 526 mounted for rotational movement relative to the distal end 528 of the bore portion 436. The mounting of the manipulator barrel 526 is achieved through an annuler flange 530 retained in a corresponding dimensioned annular chamber 532 formed adjacent the distal end 528 of the bore portion 436. An axial bore 534 extends through manipulator barrel 526 and defines a proximal region 536 and a distal region 538. Distal region 538 is formed with an internally threaded area 540, while the proximal region 536 is dimensioned for housing a translating cylindrical drive member 542. A cylindrical drive member 542 is disposed substantially within the proximal region 536 of axial bore 434 and is adapted and configured for travelling in an axial direction in response to rotation of the manipulator barrel 526.

The proximal end 546 of cylindrical drive member 542 is provided with a key slot 548 dimensioned for engagement with keys 550 and 552 of corresponding screw retainers 554 and 556. The outer cylindrical surface of each screw retainer 554, 556 is provided with elongated standoffs 558 and 560 configured to be slidably disposed in corresponding elongated slots 562 and 564 provided in the bore portion 436 of handle sections 424 and 426.

Referring to FIGS. 12 and 13, the intermediate region 566 of drive member 542 is provided with threads 543 being dimensioned to threadingly engage the internally threaded area 540 of the manipulator barrel 526. The proximal end 472 of the outer tubular section 450 is engagably retained in an axial passageway 568 extending through cylindrical drive member 542 by a lance connection 570. Thus, progressive rotation of manipulator barrel 526 will cause corresponding longitudinal movement of drive member 542 through translation of threaded portions 540 and 543 thereby causing the outer tubular section 450 to reciprocate between a proximal position and a distal position, resulting in the tool assembly 416 being articulated within a 80° angular sector.

Referring to FIG. 9, the operation of the cooperating jaws 498, 500 of tool assembly 416 is accomplished by moving the pivoting handle 434 in the direction indicated by arrow "A". The movement of pivoting handle 434 causes the head 462 of center rod 444 to translate axially, causing cable 478 and piston 490 to move in correspondence therewith. To close the cooperating jaws 498 and 500, the pivoting handle 434 is squeezed by the surgeon, causing center rod 444 to pull cable 478 in a proximal direction. The movement of cable 478 causes a corresponding axial movement of piston 490 in clevis 488. The movement of piston 490 causes pin 496 to cam proximally within slots 502 and 504, respectively, causing cooperating jaws 498,500 to close.

Progressive articulation of tool assembly 416 with respect to the longitudinal axis of elongated body portion 414 is achieved by rotating the manipulator barrel 526 in the direction indicated by arrow "B". At such a time, the outer tubular section 450 is drawn proximally as indicated by arrow "C" as the cylindrical drive member 542 is pulled rearwardly by threaded drive screw 544. The proximal retreat of outer tubular section 450 permits the articulating member 480 to relax from its stressed condition therein urging the tool assembly 416 to comply along the angular path indicated by arrow "D".

Rotation of the tool assembly 416 about the longitudinal axis of the elongated body portion 414 is achieved through manual rotation of rotatable collar 422 indicated by arrow "E". Moreover, progressive rotation of collar 422 in a clockwise direction will effectuate remote rotation of tool assembly 416 in a clockwise direction, while progressive rotation of collar 422 in a counter-clockwise direction will effectuate remote rotation of tool assembly 416 in a counter-clockwise direction.

Figure 14:
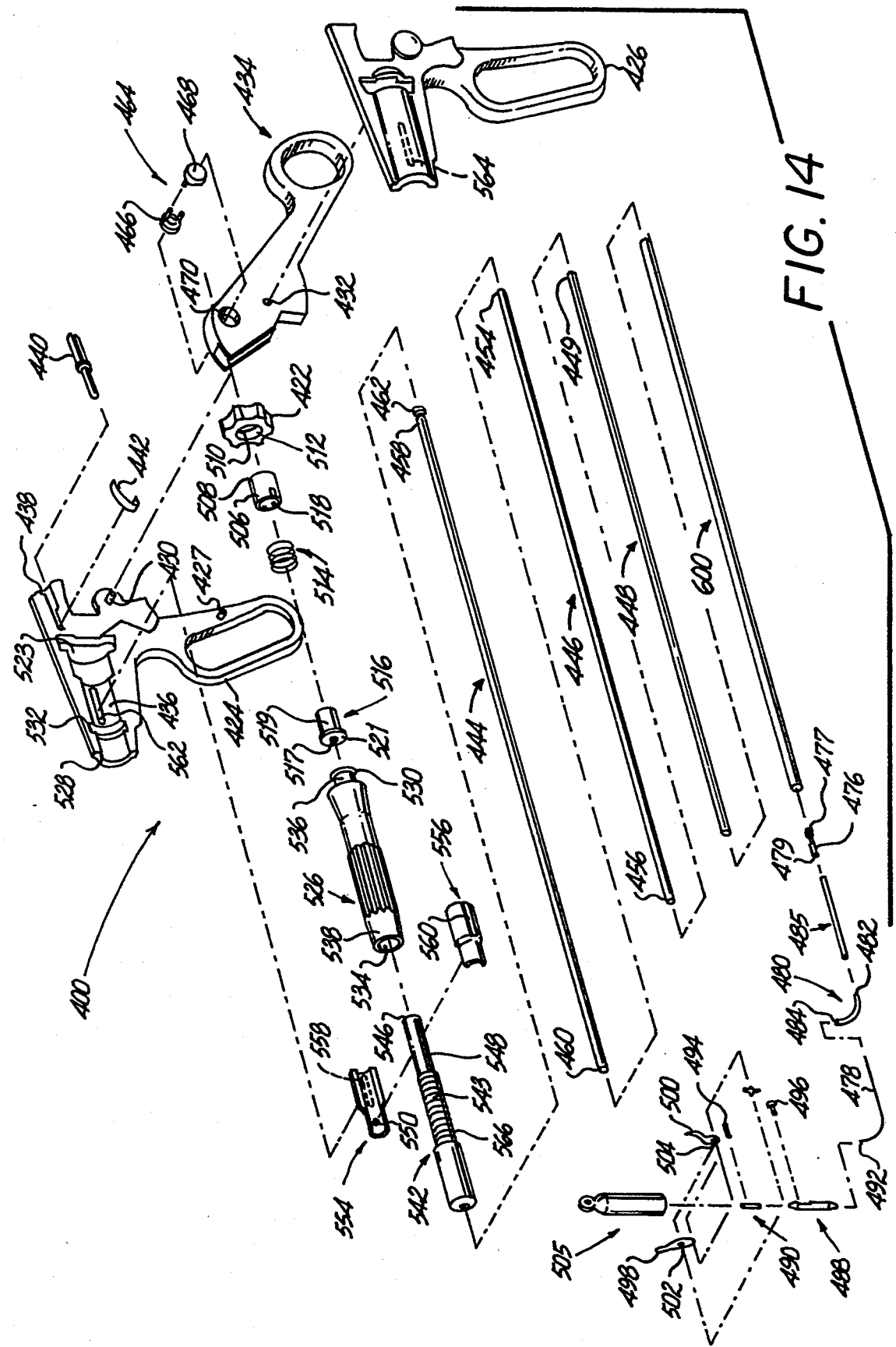
FIG. 14 is an exploded perspective view of an alternate embodiment of the articulating endoscopic surgical instrument of FIG. 9.

In a further embodiment of the invention and as shown in FIG. 14, outer tubular section 600 is fabricated from an electrically non-conductive material, e.g., a vinyl ester resin with unidirectional and circ wrap E fiberglass from Polygen Company (PGP-552), thereby obviating the need for an outer shrink wrap tube. Outer tubular section 600 exhibits sufficient rigidity and tensile strength to achieve the desired straightening of articulating member 480, while also protecting patient and user from current leakage during an electrocauterization procedure.

The endoscopic surgical instrument of the subject invention is compact, lightweight and easy to use. It is intended to enable the surgeon, after the working members are articulated to the desired orientation, to use the instrument with one hand, thus freeing the other hand for performance of surgical tasks.

Although the endoscopic surgical instrument of the subject invention has been described with respect to a preferred embodiment, it is apparent that changes may be made to the invention without departing from the spirit and scope of the invention as defined by the appended claims.

What is claimed is:

1. A surgical apparatus comprising:
   a handle portion;
   a tubular body portion extending from said handle portion and defining a longitudinal axis, said tubular body portion including an inner electrical insulating member and an outer electrical insulating member;
   a tool assembly associated with a distal end portion of said tubular body portion, said tool assembly including a tool base portion and tool means;
   connector means in association with said handle portion for delivering an electrical current to said tool assembly;
   means for effectuating remote articulation of said tool assembly between a first position substantially parallel to said longitudinal axis of said body portion and a second position substantially angularly disposed with respect to said longitudinal axis of said body portion; and
   means for effectuating remote rotation of said tool assembly about the longitudinal axis of said body portion relative to said handle assembly, wherein said means for effecting remote rotation comprises a rotation assembly including an axially rotatable collar member associated with said handle portion, and an outer tubular member extending from said collar member, through said body portion, to said tool assembly.

2. A surgical apparatus as recited in claim 1, wherein said inner insulating member is defined by a tubular member.

3. A surgical apparatus as recited in claim 2, wherein said inner insulating tubular member is constructed from a plastic electrical insulating material.

4. A surgical apparatus as recited in claim 1, wherein said outer insulating material consists of shrink wrap.

5. A surgical apparatus as recited in claim 1, wherein said tool assembly is provided with an electrical insulating member.

6. A surgical apparatus as recited in claim 5, wherein said electrical insulating member is defined by a tubular configuration.

7. A surgical apparatus as recited in claim 1, wherein said tool means comprises a pair of cooperating jaw members configured and dimensioned for use in remote suturing of tissue.

8. A surgical apparatus as recited in claim 7, further comprising actuation means extending from said handle assembly to said tool assembly for remotely moving said cooperating jaw members between an open position and a closed position.

9. A surgical apparatus as recited in claim 1, wherein said means for effecting remote articulation comprises a resilient articulator tube having a preformed angular configuration and interconnecting said tool assembly to said distal end portion of said body portion, an elongated outer tubular section axially movable with respect to said articulator tube, and an axial drive screw assembly for effectuating progressive movement of said outer tube relative to said articulator tube.

10. A surgical apparatus as recited in claim 9, wherein said resilient articulator tube is formed of a shape memory alloy.

11. A surgical apparatus as recited in claim 1 wherein said first and second positions of said tool assembly are disposed within an angular sector of rotation extending through about 0° to 90° from said longitudinal axis.

12. A surgical apparatus as recited in claim 11 wherein said angular sector of rotation extends through about 0° to 80° from said longitudinal axis.

13. A surgical apparatus comprising:
a handle portion having a fixed handle and a pivoting handle;
an elongated endoscopic portion including a fixed inner tubular section depending from said handle portion, and an outer tubular section mounted for coaxial reciprocating movement with respect to said fixed inner tubular section;
a resilient articulating member extending from said fixed inner tubular section movable in response to reciprocating movements of said outer tubular section between a first unstressed position wherein a distal portion thereof is disposed at an angle to said elongated endoscopic portion and a second stressed position wherein a distal portion thereof is substantially coaxial with said elongated endoscopic portion;
a pair of cooperating jaws operatively connected to the distal portion of said resilient articulating member;
connector means associated with said handle portion for delivering an electrical current to said cooperating jaws;
first insulator means being disposed between said fixed inner tubular section and said outer tubular section for preventing direct electrical contact between said inner tubular section and said outer tubular section;
means associated with said handle portion and said endoscopic portion for rotating said articulating member about the longitudinal axis of said elongated endoscopic portion with respect to said handle portion, wherein said rotation means includes an annular collar, whereby the proximal end of said fixed inner tubular section is operatively associated with said annular collar; and
a cable assembly for operatively connecting said cooperating jaws and said pivoting handle, whereby movement of said pivoting handle causes said cooperating jaws to open and close.

14. A surgical apparatus as recited in claim 13, wherein said outer tubular section is provided with shrink wrap.

15. A surgical apparatus as recited in claim 13, wherein said resilient articulating member is provided with second electrical insulation means.

16. A surgical apparatus as recited in claim 15, wherein said second electrical insulation means is a tubular member with said articulating member extending through said second electrical insulating tubular member.

17. A surgical apparatus as recited in claim 13, wherein said first insulator means is a tubular member configured such that said inner tubular member extends through said first electrical insulating tubular member.

18. A surgical apparatus as recited in claim 13, wherein said resilient articulating member is of tubular configuration and is formed from a shape memory alloy.

19. A surgical apparatus comprising:
a handle portion having a fixed handle and a pivoting handle;
an elongated endoscopic portion including a fixed inner tubular section depending from said handle portion, and an outer tubular section mounted for coaxial reciprocating movement with respect to said fixed inner tubular section;
a resilient articulating member extending from said fixed inner tubular section movable in response to reciprocating movements of said outer tubular section between a first unstressed position wherein a distal portion thereof is disposed at an angle to said elongated endoscopic portion and a second stressed position wherein a distal portion thereof is substantially coaxial with said elongated endoscopic portion;
a pair of cooperating jaws operatively connected to the distal portion of said resilient articulating member;
connector means associated with said handle portion for delivering an electrical current to said cooperating jaws;
first insulator means being disposed between said fixed inner tubular section and said outer tubular section for preventing direct electrical contact between said inner tubular section and said outer tubular section;
means associated with said handle portion and said endoscopic portion for rotating said articulating member about the longitudinal axis of said elongated endoscopic portion with respect to said handle portion; and
a cable assembly for operatively connecting said cooperating jaws and said pivoting handle, whereby movement of said pivoting handle causes said cooperating jaws to open and close, wherein said handle portion further includes a manipulator barrel assembly for effectuating said resilient articulating member to translate from said first unstressed position to said second stressed position in correspondence with rotational movement of said manipulator barrel.

20. A surgical apparatus as recited in claim 19, wherein said pair of cooperating jaws are pivotally connected by an electrically isolated pivot pin.

21. A surgical apparatus as recited in claim 20, wherein said pivot pin is electrically isolated by an electrically insulating bushing.

22. A surgical apparatus as recited in claim 20, wherein said pivot pin is fabricated from a dielectric material.

23. A surgical apparatus as recited in claim 22, wherein said dielectric material is selected from the group consisting of ceramics and plastics.

24. A surgical apparatus comprising:
a handle portion having a fixed handle and a pivoting handle;
an elongated endoscopic portion including a fixed inner tubular section depending from said handle portion, and an outer tubular section mounted for coaxially reciprocating movement with respect to said fixed inner tubular section, said elongated endoscopic portion further including an electrical insulating tubular section in association with said inner tubular section and said outer tubular section;

a resilient articulating member extending from said fixed inner tubular section movable in response to said reciprocating movements of said outer tubular section between a first unstressed position wherein a distal portion thereof is disposed at an angle to the longitudinal axis of said endoscopic portion and a second stressed position wherein a distal portion thereof is substantially coaxial with said endoscopic portion;

a pair of cooperating jaws operatively connected to said distal portion of said articulating member;

connector means in association with said handle portion for delivering an electrical current to said cooperating jaws;

a cable assembly for operatively connecting said cooperating jaws and said pivoting handle;

linkage means associated with said handle portion for reciprocating said outer tubular section in an axial direction with respect to said inner tubular section between said first position and said second position;

insulation means associated with said articulating member; and rotation means associated with said handle portion and said endoscopic portion for rotating said articulating member about the longitudinal axis of said elongated endoscopic portion with respect to said handle portion wherein said rotation means includes an annular collar and an annular bushing disposed concentrically within said annular collar for receiving the proximal end of said inner tubular section.

25. A surgical apparatus as recited in claim 24, wherein said insulation means is of a tubular configuration.

26. A surgical apparatus as recited in claim 24, wherein said articulating member is of tubular configuration and is formed from a shape memory alloy.

27. A surgical apparatus as recited in claim 24, wherein insulation means are associated with said outer tubular section to electrically and thermally insulate the user from said outer tubular section.

28. A surgical apparatus as recited in claim 27, wherein said insulation means consists of shrink wrap.

29. A surgical apparatus comprising:

a handle portion having a fixed handle and a pivoting handle;

an elongated endoscopic portion including a fixed inner tubular section depending from said handle portion, and an outer tubular section mounted for coaxially reciprocating movement with respect to said fixed inner tubular section, said elongated endoscopic portion further including an electrical insulating tubular section in association with said inner tubular section and said outer tubular section;

a resilient articulating member extending from said fixed inner tubular section movable in response to said reciprocating movements of said outer tubular section between a first unstressed position wherein a distal portion thereof is disposed at an angle to the longitudinal axis of said endoscopic portion and a second stressed position wherein a distal portion thereof is substantially coaxial with said endoscopic portion;

a pair of cooperating jaws operatively connected to said distal portion of said articulating member;

connector means in association with said handle portion for delivering an electrical current to said cooperating jaws;

a cable assembly for operatively connecting said cooperating jaws and said pivoting handle;

insulation means associated with said articulating member; and, articulation means associated with said handle portion and said outer tubular section for effectuating said coaxially reciprocating movement of said outer tubular section with respect to said fixed inner tubular section.

30. A surgical apparatus as recited in claim 29, wherein said articulation means comprises an axial drive screw assembly.

31. A surgical apparatus as recited in claim 29, wherein said first and second positions of said articulating member are disposed within an angular sector of rotation extending through about 0° to 90° from said longitudinal axis.

32. A surgical apparatus as recited in claim 29, wherein said pair of cooperating jaws are pivotally connected by an electrically isolated pivot pin.

33. A surgical apparatus comprising:

a handle portion having a fixed handle and a pivoting handle;

an elongated endoscopic portion including a fixed inner tubular section depending from said handle portion, and an outer tubular section mounted for coaxial reciprocating movement with respect to said fixed inner tubular section, said outer tubular section being fabricated from an electrically nonconductive material;

a resilient articulating member extending from said fixed inner tubular section movable in response to reciprocating movements of said outer tubular section between a first unstressed position wherein a distal portion thereof is disposed at an angle to said elongated endoscopic portion and a second stressed position wherein a distal portion thereof is substantially coaxial with said elongated endoscopic portion;

a pair of cooperating jaws operatively connected to the distal portion of said resilient articulating member;

connector means associated with said handle portion for delivering an electrical current to said cooperating jaws;

means operatively associated with said handle portion and said endoscopic portion for rotating said articulating member about the longitudinal axis of said elongated endoscopic portion with respect to said handle portion; and means for operatively connecting said cooperating jaws and said pivot handle, whereby movement of said pivoting handle causes said cooperating jaws to open and close, wherein said rotation means includes an annular collar, whereby the proximal end of said fixed inner tubular section is operatively associated with said annular collar.

34. A surgical apparatus as recited in claim 33, wherein said resilient articulating member is of tubular configuration and is formed form a shape memory alloy.

35. A surgical apparatus comprising:

a handle having a fixed handle and a pivoting handle;

an elongated endoscopic portion including a fixed inner tubular section depending from said handle portion, and an outer tubular section mounted for coaxial reciprocating movement with respect to said fixed inner tubular section;

a resilient articulating member extending from said fixed inner tubular section movable in response to reciprocating movements of said outer tubular section between a first unstressed position wherein a distal portion thereof is disposed at an angle to said elongated endoscopic portion and a second stressed position wherein a distal portion thereof is substantially coaxial with said elongated endoscopic portion;

a pair of cooperating jaws operatively connected to the distal portion of said resilient articulating member;

means operatively associated with said handle portion and said endoscopic portion for rotating said articulating member about the longitudinal axis of said elongated endoscopic portion with respect to said handle portion; and means for operatively connecting said cooperating jaws and said pivot handle, whereby movement of said pivoting handle causes said cooperating jaws to open and close, wherein said handle portion further includes a manipulator barrel assembly for effectuating said resilient articulating member to translate from said first unstressed position to said second stressed position in correspondence with rotational movement of said manipulator barrel.

36. A surgical apparatus as recited in claim 35, wherein said manipulator barrel assembly further includes an axial drive screw assembly.

* * * * *